(12) United States Patent
Mytelka

(10) Patent No.: US 6,342,362 B1
(45) Date of Patent: Jan. 29, 2002

(54) METHODS AND COMPOSITIONS FOR THE PURIFICATION OF PROTEINS OR OTHER MACROMOLECULES

(76) Inventor: Daniel S. Mytelka, 12280 Creekwood La., Carmel, IN (US) 46032

( * ) Notice: Subject to any disclaimer, the term of this patent is extended or adjusted under 35 U.S.C. 154(b) by 0 days.

(21) Appl. No.: 09/628,776

(22) Filed: Jul. 29, 2000

Related U.S. Application Data

(60) Provisional application No. 60/147,257, filed on Aug. 5, 1999.

(51) Int. Cl.$^7$ .................. G01N 33/53; G01N 33/00; G01N 33/566; C07H 21/00
(52) U.S. Cl. .................. 435/7.1; 436/94; 436/501; 536/25.4
(58) Field of Search .................. 435/6, 7.1, 810; 436/94, 501, 63; 536/25.4

(56) References Cited

U.S. PATENT DOCUMENTS

| | | | | |
|---|---|---|---|---|
| 5,011,770 A | * | 4/1991 | Kung et al. | 435/6 |
| 5,539,094 A | * | 7/1996 | Reed et al. | 536/23.5 |
| 5,700,921 A | * | 12/1997 | Westling et al. | 536/22.1 |
| 5,714,371 A | * | 2/1998 | Ramanathan et al. | 435/219 |
| 5,753,439 A | * | 5/1998 | Smith et al. | 435/6 |
| 6,124,092 A | * | 9/2000 | O'Neill et al. | 435/6 |

* cited by examiner

*Primary Examiner*—Kenneth R. Horlick

(57) ABSTRACT

The present method relates to improvements in methods for the purification of proteins and other macromolecules. In particular, the invention relates to the use of a tag to permit the facile repurification of a previously purified macromolecule, after the tagged macromolecule has been allowed to interact with other compositions. These methods can be useful in the modification of macromolecules and in screens involving macromolecules, as well as for the purification of portions of an isolated macromolecule.

5 Claims, No Drawings

METHODS AND COMPOSITIONS FOR THE PURIFICATION OF PROTEINS OR OTHER MACROMOLECULES

This application claims the benefit of U.S. Provisional Application No. 60/147,257, filed Aug. 5, 1999.

BACKGROUND OF THE INVENTION

The present invention relates to improvements in methods for the purification of macromolecules. In particular, it relates to methods for purifying macromolecules that have been added to a solution in order to carry out some desired purpose, but whose continuing presence is not desired. For example, a protease might be added during a step in the commercial production of an important product (e.g. blood factor VIII for hemophilia), but its removal might be necessary to carry out a subsequent step or to produce a sufficiently pure product for medicinal uses.

There are a large number of procedures that have traditionally been used to separate macromolecules, such as various chromatographic separations (by size, charge or affinity). These methods are generally time consuming, and appropriate methods vary with the target product and the identity of the contaminants. Proteins that have been genetically modified to have a run of histidines (a histidine tag) can be purified relatively simply on a nickel column (Hochuli et al.(1984), *J. Chromat.* 411:177; Porath (1992), *Protein Exp. Purif.* 2:263), and a number of companies (such as NOVAGEN, QIAGEN and InVitrogen) have designed systems for overexpressing such proteins and purifying them. These tagged proteins can also be attached to substrates for convenient manipulation, and can be repurified if desired. Proteins that have purified by other means, however, are less easily manipulated. For example, the enterokinase (a protease) cleavage site is often engineered into proteins in order to permit the removal of N-terminal sequences used in purification, but there is no straightforward procedure for quantitatively removing the enterokinase following the reaction. The absence of a general method for removing proteins (or other macromolecules) that have been added to a mixture puts a substantial constraint on the usefulness of many molecules.

SUMMARY OF THE INVENTION

This invention provides a means for removing a macromolecule (such as a protein molecule) from a mixture to which the purified macromolecule has been added. The macromolecule is modified by the addition of a tag following purification, and the tag can be used to remove the macromolecule once its purpose has been accomplished. In the preferred embodiment of this invention, a linking agent is used in which one portion of the linking agent comprises a tag that can be used for purification, while another portion of the linking agent comprises an active group that can bind to various parts of a macromolecule. For example, a linking agent can be made that consists of the maleimide group connected by a flexible carbon chain to six histidine residues. This linking agent can be used to attach the histidine tag to —SH or —NH$_2$ groups of macromolecules (such as the side chain of cysteine).

This invention also comprises the linking agents that can be used in the above procedure to repurify a macromolecule. In addition, kits are envisioned that contain materials for performing the above purification, such as a kit containing a linking agent, a compatible purification system, and additional reagents and instructions as necessary. For example, a kit might comprise the maleimide/his-tag linking agent described supra plus material for preparing a nickel column for purification. Alternatively, the nickel column might be replaced by a syringe containing a similar purification matrix, so the mixture containing the maleimide/his-tag modified protein and other components can be purified by pushing it through the syringe.

In some situations, it might be necessary to purify the modified protein away from the unreacted linking agent in order to prevent the linking agent from reacting with other components of the mixture to which the modified protein is to be added. This may be accomplished by a size separation or by using a relatively low ratio of linking agent to target and purifying the target protein using the tag. These two procedures could be combined such that a target is first reacted with an excess of linking agent and separated from the unreacted linking agent by size, and the target population is then purified using the tag to ensure that all molecules are tagged. Batches that have been prepared in this fashion can in turn form the nucleus of kits. For example, a kit might comprise a protease that has been tagged in this fashion plus a purification system and appropriate additional reagents and instructions.

DEFINITIONS

Terms herein generally follow their normal, accepted meanings in the art, and may be found in any of the common text books or laboratory manuals, such as *Biochemistry* (Lehninger, Worth Publishers, 1975), *Biochemistry* (Stryer, W.H.Freeman and Company, 1988), *Molecular Cloning: A Laboratory Manual* (Sambrook et al., Cold Spring Harbor Press, 1989), *Current Protocols in Molecular Biology* (Ausubel et al., Wiley Interscience, 1994) and *Chemistry of Protein Conjugation and Cross-Linking* (Wong, CRC Press, 1991).

The term "linking agent", as used herein, refers to a non-naturally occurring molecule comprising a tag and a binding region. In some unusual implementations, these regions could overlap.

The term "tag", as used herein, refers to a molecule that can be attached to a larger macromolecule, and which can be used to separate that macromolecule from macromolecules that do not have the tag.

The term "binding region", as used herein, refers to the region of a linking agent that can attach the linking agent to specific regions of macromolecules under appropriate conditions. The attachment will generally be covalent, but need not be, though it must be strong enough so that there will not be a substantial amount of separation during purification.

DETAILED DESCRIPTION

A. Designing Appropriate Linking Agents

Linking agents are created by combining appropriate tags and binding regions. Tags and binding regions are well known to those of ordinary skill in the art, though they have never been used for the sorts of purposes envisioned herein. While the applications described herein use known tags and binding regions as exemplars, there is no reason why any newly discovered tag or binding region would not be comparably appropriate.

Tags are typically used in the isolation of proteins. For this purpose, the DNA that encodes the tag is usually attached to one of the ends of the corresponding cloned gene, which causes the expressed gene to produce a tagged protein product suitable for isolation. Commonly used tags include runs of histidines ("his-tag"), portions of glutathione S-transferase ("GST-tag") and a variety of short sequences that can be recognized by antibodies. Some such tags are described in catalogs from laboratory suppliers, such as NOVAGEN, InVitrogen and QIAGEN. Important features of a tag include its ability to facilitate purification (such as by binding tightly to an appropriate column or antibody), its ability to fold reasonably independently, and its lack of interference with the function of the tagged protein. Since the tags envisioned herein will attach to a variety of positions on a protein, it is likely that many of these attachments will have little effect on the function of the protein, which is a substantial improvement over the conventional method in which a tagged protein is produced from a cloned gene, with the tag being present in a specific position that might well cause problems. Methods for purifying proteins that have one of these tags attached are well known to those of ordinary skill in the art.

Binding regions are well known in the literature concerned with creating bifunctional molecules that will act as cross-linking agents. For example, Wong provides a wealth of information on designing and selecting appropriate molecules (see Wong, *Chemistry of Protein Conjugation and Cross-Linking*, CRC Press, 1991 and references therein). An appropriate choice is typically a binding region that reacts relatively non-specifically with the target molecule, but does not react with any component of itself (a binding region that reacts with histidine side chains, for example, would not typically be considered a good choice when using a his-tag, though such a reaction could produce very strong signals akin to the self-reactions in the ubiquitination pathway). Commonly used agents suitable for use as binding regions include aryl halides (which react with histidine side chains), N-maleimide derivatives (react with —SH and —$NH_2$), mercurials (react with —SH), disulfides (react with —SH), acid anhydrides (react with —$NH_2$ and phenols), isocyanates (react with —$NH_2$), isothiocyanates (react with —$NH_2$), sulfonyl halides (react with —$NH_2$), imidoesters (react with —$NH_2$), diazoacetates (react with —COOH and —SH) and dicarbonyl compounds (react with —NH—C(NH)—$NH_2$). Appropriate reactions conditions for using these binding regions are well known to those of ordinary skill in the art.

In designing a linking agent, it is important to consider both desired internal and external characteristics. Internally, it is important to choose tags and binding regions that work well together, ones that do not interact with each other in order to lessen desired functionality. In addition, it is important to maintain an appropriate distance between these two components so that both are able to operate simultaneously. For example, a carbon chain linker could be incorporated between the two regions (such as (N-substituted) maleimide —$(CH_2)_6$-$his_6$), in order to allow the his-tag to be sufficiently far from the target molecule such that binding of the linking agent to a target molecule does not sterically interfere with the ability of the tag to bind to a nickel column. Desirable external characteristics include selecting a binding region that will bind with a desired specificity to the target macromolecule, and choosing a tag that will appropriately facilitate purification. In some cases, it might be desirable to create a linking agent that will bind reversibly to a target protein. For example, the use of a binding agent that forms disulfide bonds with cysteines could be reversed in the presence of a reducing agent such as DTT.

Linking agents can be made by essentially the same techniques currently used to make cross-linking agents, except that pertinent reactions will take place between a tag and a linking region instead of between two linking regions (some cross-linking agents are heterobifunctional, so it is not unusual to perform the pertinent condensation or other reaction between two different types of molecules). These reactions are well known to those of ordinary skill in the art, and will vary somewhat (as far as blocking groups and appropriate conditions) depending on the identity of the tag and the linking region. For a maleimide-his-tag linking agent in particular, it might be additionally possible to make the linking agent by performing solid phase protein synthesis (Merrifield et al. (1963), J. Am. Chem. Soc. 85:2149) using histidines and N-carboxylate-maleimide.

B. Using Linking Agents

The essential purposes of a linking agent are to isolate a particular component from a complex solution or to bind that component to a particular matrix. For either purpose, one must first isolate the component that one wants to use by conventional means, such as by column chromatography. These purifications will follow the methods that are standard in the art for purification of the relevant molecule. Following the purification, the macromolecule is reacted with a linking agent in order to tag it; this reaction is performed using the conditions that are well known in the art for the binding agent. For example, a reaction involving a linking agent comprising a maleimide-based binding region might use a neutral to mildly acidic pH, a 0.1 M sodium phosphate buffer and a temperature of 20° C., which is one set of conditions frequently used with maleimide cross-linking agents. The appropriate ratio of linking agent to target will vary based on the particular combination used, but will be easily determined by routine experimentation. It will typically be useful to use an excess of linking agent in order to ensure that most target molecules are labeled, but it might be useful in particular instances to use less, either for the reasons stated supra or because the target molecule might have a critical site that is a potential target for the binding agent (in which case excess linking agent might lead to undesirable levels of target inactivation, while lower levels might lead to mostly active product). If lower ratios of linking agent are used, it will generally be useful to purify labeled product from unlabeled product, and (if appropriate) assay the activity level of the labeled product.

Isolation is important when it is desirable to have the component in question present at a particular time, but absent subsequently. For example, it might be desirable to have a restriction endonuclease present in order to cleave a particular DNA molecule, but it might be desirable to remove it before introducing another DNA molecule for cloning. While extractions and heat inactivation are usable in many cases, some endonucleases are resistant to heat inactivation, and it may be too slow or undesirable to do an extraction for other reasons. Taq DNA polymerse is resistant to both extraction and heat inactivation, and neither treatment will be effective if the component whose removal is desired is another DNA molecule, such as a carrier nucleic acid or an unreacted parent DNA molcule (see Example 2). In all cases, however, a linking agent can be used to specifically remove the target molecule from the mixture. This can be carried out by adding the linking agent/bound target molecule to the mixture, allowing the desired reactions to occur, then removing the tag (and thus the bound target molecule). If the tagged molecule is the molecule of interest, it can be added to a mixture and then repurified to see whether any of the components of the mixture are able to act on the protein, such as a kinase in the mixture phosphorylating a protein.

It can be desirable in some instance to bind a target molecule to a particular substrate. For research purposes, it is often desirable to attach a molecule to some substrate and determine what other molecules bind to that molecule; this can be facilitated using a linking agent to attach a tag to the target molecule, allowing it to be bound to an appropriate matrix. For example, a newly isolated protein can be reacted with a linking agent containing a his-tag, and the resulting conjugate can be attached to a nickel column. This method can be useful in screens for interesting compounds (such as compounds that might act on an oncogenic protein or bind to a piece of DNA (similar to a Southern hybridization, but in solution)). This is simpler than many existing methods and has the additional advantage of being more general in certain ways: a protein bound by a traditional means (such as an antibody) will always expose the same surface, while a linking agent method can provide molecules bound in heterogeneous fashions. In addition, these methods can be used in diagnostic assays, such as in running a blood sample over a bound protein/antibody to see if there are any antibodies/proteins in a blood sample bind, indicating the presence of a particular disease.

The materials, products, methods and examples described herein are illustrative only and not limiting, Numerous variants will immediately be apparent to one of ordinary skill in the art upon understanding the basic invention, and are meant to be included within the scope of this invention. All publications mentioned herein are incorporated by reference, as are references cited within those documents that provide elucidation of the techniques and knowledge that are readily available to one of ordinary skill in the art, particularly in regard to reaction conditions, purification techniques and synthetic methods.

The products and methods described herein can be done using various stringencies, ratios, improvement factors, temperatures, concentrations, times, lengths, sizes, masses, molecular weights, areas, volumes, binding constants and so on. Depending on the particular application, ranges envisioned include from negative infinity to positive infinity and any subrange thereof. In particular, ranges envisioned include above, below or equal to any of the following: −1000000, −100000, −10000, −5000, −2000, −1000, −500, −200, −100, −70, −50, −20, −10, −5, −2, −1, 0, 0.000000000000001, 0.00000000000001, 0.0000000000001, 0.000000000001, 0.00000000001, 0.0000000001, 0.000000001, 0.00000001, 0.0000001, 0.000001, 0.00001, 0.0001, 0.001, 0.01 , 0.1, 0.2, 0.4, 0.5, 0.75, 1, 1.5, 2, 2.5, 3, 4, 5, 6, 7, 8, 9, 10, 11, 12, 13, 14, 15, 16, 18, 20, 22, 25, 30, 32, 35, 37, 40, 42, 45, 50, 55, 60, 65, 70, 75, 80, 90, 100, 110, 120, 130, 140, 150, 175, 200, 250, 300, 350, 400, 450, 500, 600, 700, 800, 900, 1000, 1500, 2000, 3000, 4000, 5000, 7500, 10000, 12500, 15000, 17500, 20000, 25000, 30000, 40000, 50000, 60000, 70000, 75000, 80000, 90000, 100000, 125000, 150000, 175000, 200000, 250000, 300000, 400000, 500000, 750000, 1000000, 1500000, 2000000, 3000000, 5000000, 10000000, 20000000, 30000000, 50000000, 100000000, 250000000, 500000000, 1000000000, 10000000000, 100000000000, 1000000000000. In addition, ranges could be between any two of those numbers. Guidance as to what ranges are appropriate in a particular instance come from publications cited herein and/or are well known to those of ordinary skill in the art.

EXAMPLES

Example 1
Purification of a Protein Following Proteolysis

This example describes a method for purifying the protein for human insulin. The gene for human insulin has been cloned, and current methods are available to produce the protein in cells and purify the resulting protein. If the protein is to be usable in humans, it should be identical to the natural form of the protein, but it would be simpler to produce the protein in a recombinant form that contains a tag that facilitates its purification. For example, the protein could be produced with an N-terminal his-tag, permitting purification on a nickel column. In order to remove the his-tag, an enterokinase cleavage site could be incorporated following the his-tag; the enterokinase protease cleaves at the C-terminus of its cleavage site, so its cleavage regenerates the native protein, subject to possible changes in glycosylation or other modification.

A)React purified enterokinase protein with a linking agent comprising a maleimide binding group and a his-tag as a tag. Purify tagged protease on a nickel column. NB: If the enterokinase gene was cloned, this step could be carried out by creating recombinant enterokinase proteins directly, inserting a region encoding a his-tag into the enterokinase gene.
B)Modify the cloned insulin gene to encode an N-terminal extension comprising a his-tag followed by an enterokinase cleavage site. Produce large quantities of this protein and purify on a nickel column, producing a pure solution of tagged insulin molecules.
C)Mix the tagged protease with the tagged insulin molecule, allowing the protease to cleave the tagged region from the insulin protein. NB: Make sure that the protease does not cleave in the mature region of the desired protein product.
D)Purify the resulting mixture over a nickel column. The tagged protease will stick to the column, as will the uncleaved insulin molecules and the tags cleaved off the insulin molecules; only native insulin molecules will flow through the column.

Example 2
Isolating a Desired DNA Fragment

This example describes a method for isolating a DNA fragment from a vector containing that fragment. Commonly used current methods generally involve gel electrophoresis followed by isolation of the desired DNA fragment from the gel; these methods are laborious and lead to loss of a substantial fraction of the sample.

A)React purified DNA binding protein (such as lac repressor) with a linking agent comprising a maleimide binding region and a his-tag. Purify the tagged protein on a nickel column. NB: For cloned DNA binding proteins, the his-tag can be incorporated by modifying its DNA to contain a region encoding a his-tag; this will create a linking agent wherein the binding region is the DNA binding region of the protein and the tag is the incorporated his-tag and the connecting region consists of additional protein.
B)React the tagged DNA binding protein with a DNA molecule containing the cognate DNA binding site and the insert of interest, with the DNA binding site being present within the vector sequences. If desired, purify the protein/DNA complexes over a nickel column, or permit them to bind to a nickel column, in order to eliminate unreacted plasmids. NB: It is also possible to follow this procedure using a linking agent comprising a binding region that binds directly to DNA, such as an intercalating agent, but it will generally be difficult to achieve sufficient specificity for the vector region.
C)Cleave the plasmid with appropriate enzymes to release the insert of interest as a single fragment, with the remaining fragment being the protein/DNA complex.
D)Pass the mixture over a nickel column to remove vector sequences, which will bind the column. The pure insert will flow through.

I claim:

1. A method for separating macromolecules comprising:
   A) Mixing a chemical composition comprising a binding region and a tag with a target macromolecule so the binding region binds to the target macromolecule;
   B) Optionally purifying the composition-target complex;
   C) Mixing the composition-target complex with other composition(s);
   D) Incubating the mixture such that a desired chemical reaction occurs;
   E) Removing the composition-target complex from the mixture by selectively removing molecules having the tag.

2. A method for separating macromolecules comprising:
   A) Mixing a chemical composition comprising a binding region and a tag with a target macromolecule so the binding region binds to the target macromolecule;
   B) Optionally purifying the composition-target complex;
   C) Mixing the composition-target complex with other composition(s);
   D) Incubating the mixture such that the composition-target complex binds to other protein composition(s);
   E) Removing the composition-target complex from the mixture by selectively removing molecules having the tag.

3. A method for cleaving a target macromolecule comprising mixing the target macromolecule with a tagged composition that can cleave it under conditions whereby said macromolecule is cleaved, and then selectively removing said tagged composition via its tag.

4. A method for isolating a DNA fragment(s) comprising cleaving a DNA molecule to form fragments, mixing said fragments with a tagged DNA-binding protein that only binds to desired or undesired DNA fragment(s) to form a DNA-binding protein-fragment complex(es), and then selectively removing said complex(es) via the tag on the tagged DNA-binding protein.

5. The method of claim 1, wherein the target macromolecule is a protease.

* * * * *